United States Patent [19]

Ritts, Jr.

[11] 4,434,230

[45] Feb. 28, 1984

[54] HUMAN NONSECRETORY PLASMACYTOID CELL LINE

[75] Inventor: Roy E. Ritts, Jr., Rochester, Minn.

[73] Assignee: Research Corporation, New York, N.Y.

[21] Appl. No.: 292,277

[22] Filed: Aug. 12, 1981

[51] Int. Cl.³ .................. C12N 5/00; C12N 5/02; C12N 15/00; C12R 1/91
[52] U.S. Cl. .................. 435/240; 435/172; 435/948; 435/241
[58] Field of Search ........... 435/240, 241, 68, 172, 435/948; 424/85

[56] References Cited

PUBLICATIONS

Olsson et al., "Human-Human Hybridomas Producing Monoclonal Antibodies of Pre-defined Antigenic Specificity", Proceedings of the National Academy of Sciences 77(9), (1980), pp. 5429–5431.
Croce et al., "Production of Human Hybridomas Secreting Antibodies to Measles Virus" Nature 288, (12-1980), pp. 488–489.
Steel et al., "Possibility of EB Virus Preferentially Transforming a Subpopulation of Human B Lymphocytes", Nature 270, (12-1977), pp. 729–731.
Levy et al., "Rescue of Immunoglobin Secretion from Human Neoplastic Lymphoid Cells By Somatic Cell Hybridization" Proceedings of the National Academy of Sciences 75(5), (1978), pp. 2411–2415.
Newswatch, "Scots Develop New Way to Make Human Hybridomas", Monday, Jul. 6, 1981, p. 6.
Lundak et al., "Production of Human Human Secreting Specific Antibody", Abstracts of the Annual Meeting of the American Society for Microbiology, 1981, vol. 81 (9), p. 62.

Primary Examiner—Thomas G. Wiseman
Assistant Examiner—John Edward Tarcza
Attorney, Agent, or Firm—Scully, Scott, Murphy & Presser

[57] ABSTRACT

A human non-secretory plasmacytoid continuous cell line, established for five years in more than 150 passages, is karyotypically normal, easily grown and has the characteristic features of a plasmablast excepting for its secretory defect, and can be used for the preparation of human-human hybridomas with human B-lymphocytes and separation of the resulting hybridomas from the plasmacytoma cell line by growth in $CO_2$-containing media, or by fluorescence activated cell sorting, or both.

6 Claims, 2 Drawing Figures

HUMAN NONSECRETORY PLASMACYTOID CELL LINE

BACKGROUND OF THE INVENTION

1. Field of the Invention

The present invention relates to a human cell line useful for the preparation of monoclonal antibody-secreting human-human hybridomas.

2. Description of the Prior Art

The preparation of hybridoma cell lines derived by fusing a mouse myeloma cell line and mouse B-lymphocytes sensitized against a given antigen is by now well known in the art. For example, based on the original work by Kohler, G. and Milstein, C. (Nature 256:495–497 (1975); European Journal of Immunology, Vol. 6, pp. 511–519 (1976), see also Milstein, C.: "Monoclonal Antibodies", Scientific American, Vol. 243:66–74 (1980)), Koprowski et al, in U.S. Pat. No. 4,172,124 prepared somatic cell hybrids between hypoxanthine phosphoribosyl transferase (HPRT) deficient cells and spleen or lymph cells derived from a mouse previously primed with tumor cells. Koprowski et al, in U.S. Pat. No. 4,196,265, prepared continuous cell lines of genetically stable fused cell hybrids capable of producing large amounts of monoclonal antibodies against specific viruses and their antigenic determinants. The cell lines of Koprowski et al '265 are fused cell hybrids between viral antibody producing cells and myeloma cells. Wands et al, U.S. Pat. No. 4,271,145, disclose cell lines for producing monoclonal antibodies to hepatitis virus established by immunizing animal lymphocytes with hepatitis antigen to form antibody-producing cells which are then fused with myeloma cells.

The aforementioned prior art references however, disclose only hybridomas derived from non-human (in most cases mouse) myeloma and non-human lymphocyte cells.

It has been recognized (see for example Milstein, C., Scientific American supra, at 74) that for a variety of therapeutic applications, antibodies derived from human lymphocytes rather than from the mouse or the rat would be much more desirable. Although chimeric hybridomas have been obtained by fusing mouse myeloma cells with human IgG-producing cells (Levy, R. and Dilley, J., Proceedings of the National Academy of Sciences U.S.A., 75:2411–2415 (1978)), these hybrids tend to be unstable due to the fact that when human cells are fused with animal cells, there is a rapid preferential loss of human chromosomes from the resulting interspecific hybrid cells.

In fact, in October 1980, Milstein (Scientific American, supra) stated that "so far, the search for a suitable human myeloma line that can be cultured and fused to make an intraspecific hybrid has not borne fruit".

There exists a need therefore for a successful method for preparing human-human hybridoma cell lines. This need would be fulfilled with the existence of an appropriate, long surviving, pure, continuous, human cell line capable of being fused with human B-lymphocytes to produce said hybridoma lines.

SUMMARY OF THE INVENTION

It is therefore an object of the invention to provide a human cell line useful for the preparation of human-human hybridomas by fusion of said cell line with human B-lymphocytes.

It is another object of the invention to provide a human plasmacytoma cell line useful for the preparation of human-human hybridomas, which plasmacytoma cell line is sensitive to $CO_2$.

It is yet another object of the invention to provide a human plasmacytoma cell line as hereinbefore, which does not secrete immunoglobulins.

Still another object of the invention is to provide a method of preparing human-human hybridomas.

Yet another object of the invention is to provide a method of preparing human-human hybridomas which utilizes a $CO_2$ selection technique and/or the absence of surface membrane immunoglobulin receptors for the isolation of the hybridoma cell line.

These and other objects of the invention as will hereinafter become more readily apparent have been attained by providing:

A biologically pure culture of a continuous, human, non-secretory, plasmacytoid cell line having ATCC deposit #CRL-8083, as well as clones and subclones thereof.

Another object of the invention has been attained by providing:

A method of producing human-human hybridomas which comprises:

fusing a human B-lymphocyte with the aforementioned non-secretory human, continuous plasmacytoma cell line, to form an antibody-producing hybridoma.

DESCRIPTION OF THE PREFERRED EMBODIMENTS

Figure 1:
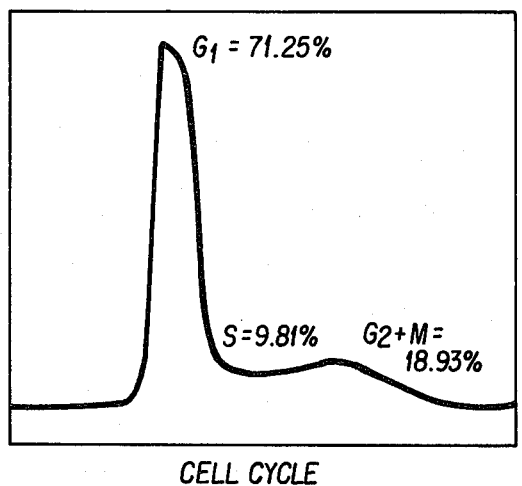
FIG. 1 shows the cell cycle of CRL-8083 using mithramycin strained cells in a fluorescence activated cell sorter. Abscissa: fluorescence intensity; Ordinate: Number of cells.

The present inventor has discovered a human plasmacytoma cell line which does not secrete immunoglobulins, which line can be cultured continuously in cell culture, which is biologically pure, free of mycoplasma, and which can be fused with human B-lymphocytes to prepare human-human hybridomas. The discovery of this plasmacytoma cell line therefore opens up the possibility of preparing stable, continuous, human-human hybridomas.

Since the plasmacytoma cell line does not secrete immunoglobulins, and the hybridomas do, the cell line, in addition, allows for the selective separation of hybridomas from the plasmacytoma, by taking advantage of this property. Also, the inventor has discovered that the plasmacytoma cell line of the invention grows well in an atmosphere of 3–5% $CO_2$ but is 85–95% killed in an environment which is 9–11% $CO_2$ or higher. This provides for yet another method of separating the hybridomas from the plasmacytoma, since the former are routinely grown in 10% $CO_2$. Finally, the present inventor has also discovered that HPRT deficient mutants of the plasmacytoma cell line of the invention can be prepared. These, therefore, provide still a third method of separating the (mutant) plasmacytoma cell line from the hybridomas, by using the well known HAT selection media.

By light microscopy, the cells of CRL-8083 have a considerable pleomorphic appearance and variation in size. The cells have a characteristic plasmacytoid appearance with pyronin/methyl green or Giemsa stain. Many of the cells are signet ring-appearing, with relatively normal nuclear cytoplasmic ratio, dark staining cytoplasm, Russell bodies, occasionally prominent hof and mitochondria. The nuclei are ovoid and eccentrically located, and atypical nucleoli are prominent. The electron microscopic morphology demonstrate the usual pleomorphic characteristics and immaturity customarily observed in normal reactive plasma cells, or even in some highly malignant forms seen in the bone marrow (see Maldonado, J. E. et al, Cancer 19:1613–1627 (1966)). The plasmacytic features evident in most of the cells are rough endoplasmic reticulum which is not well organized in lamella or a abundant as in more highly anaplastic cells. The Golgi area and prominent, often bizrre mitochondria, dense osmiophilic bodies, and vacuoles are strikingly evident, as are the ovoid, eccentric nuclei with peripheral chromatin distribution.

Histochemical staining reveals that the cells are myeloperoxidase, albumin, sudan black, and lysozyme negative (see Graham, R. C. et al, J. Histochem. Cytochem. 14:291–302 (1966); McManus, J. F. A. Nature 158:202 (1946); Li, C. Y. et al, Am. J. Clin. Pathol. 70:721–732 (1978); and McManus, supra, respectively.). A few cells were noted to be clearly PAS positive, (Sheehan, H. L. and Storey, G. W., J. Pathol. Bacteriol. 59:336–337 (1947)), but this observation has not been unequivocably confirmed. Reactivity with α-naphthyl butyrate esterase was equivocal (±) (Li, C. Y. et al, J. Histochem. Cytochem. 21:1–12 (1973)), but markedly positive with α-naphthyl acetate esterase (Yam, L. T., et al, Am. J. Clin. Pathol. 55:283–290 (1971)). The cells are also positive for β-glucuronidase (Lorbacher, P. et al, J. Histochem. Cytochem. 15:680–697 (1967)), and acid phosphatase (Li, C. Y. et al, J. Histochem. Cytochem. 18:473–481 (1970)), as well as for terminal deoxynucleotidyl transferase (TDT), determined by biochemical (Greenwood, M. F. et al, J. Clin. Invest. 59:889–899 (1977)), and immunofluourescent methods (Bollum, F. J., "Immunofluorescence in Antiviral Mechanisms in the Control of Neoplasia" (Ed. Chandra, C., Plenum Press, New York 1978)).

Repeated attempts to demonstrate surface membrane immunoglobulins with all commercially available domestic reagents, as well as with several other antisera, have failed. Similarly, studies using up to 10,000 times concentration of cell culture supernatants to detect human immunoglobulins by radioimmunoassay and enzyme immunoassay, or using the cells for a plaque assay technique also have been unsuccessful. However, cytoplasmic staining (Hijmans, W. et al, Clin. Exp. Immunol. 4:457–472 (1969)) with FITC-labeled goat polyclonal F(ab')$_2$, or mouse monoclonal anti-human IgA, IgM, IgG and IgD anti-sera specific for the heavy chains and for the κ and λ light chains, show strongly positive flourescence cytoplasmic γ and κ in 15–18% of the cells. These reactions are inhibited by the addition of unlabeled pure anti-IgG or κ prior to staining. A sandwich immunoassay method was developed in which $5 \times 10^5$ cells were fixed to the bottom of a plastic microtiter plate wells, and incubated with multiply absorbed rabbit anti-G1, G2, G3 and G4 antisera, 3 times washed, incubated with goat anti-rabbit gamma globulin anti-sera labeled with alkaline phosphatase, and then developed with p-nitrophenyl phosphate for 30 minutes. This enzyme immunoassay unequivocally demonstrates that the cells have G1 exclusively.

Ferritin labeled anti-IgG, IgM, IgA, κ and λ in electron microscopy sections and on fresh cells (Kraehenbuhl, J. P. and Jamieson, J. D., Int. J. Exp. Pathol. 13:1–53 (1974)), demonstrated no surface membrane binding, but 17% of the cells have pronounced dense vacuole staining with anti-IgG or κ reagents. These vacuoles are intensely stained either centrally or uniformly. They differ from cultures of secretory cells which, in contrast, have dense SmIg staining and more diffuse and less intense staining of Ig within the vacuoles, but with an intensity comparable to the cell line of the invention noted only at the periphery of the vacuoles.

Several surface characteristics of the cell line of the invention can also be given. There are no sheep erythrocyte receptors in the conventional (Jondal, M. et al, J. Exp. Med. 136:207–215 (1972)), or so-called active (Wybran, J. and Fundenberg, H. H. J. Clin. Invest. 52:1026–1032 (1973)) or high affinity technique (Oldham, R. K. "The Compendium of Assays for Immunodiagnosis of Human Cancer", Editor Herberman, R. D., Elsevier/North Holland, New York 1979), nor were rosettes observed with "long" (24 hour) or "short" (4 hour) incubation with mouse erythrocytes. There are not receptors for $Cl_q$ but about 23% of the cells are positive for C3b using a rosette methodology. No Fc γ receptors can be observed using rabbit IgG-coated chicken erythrocytes, although one rabbit anti-sheep antibody IgM coated sheep erythrocyte preparation did cause rosette formation. Further study with this particular antibody without sheep red blood cells demonstrates direct binding to the cell membrane, suggesting a cross-reactivity of obscure specificity. This is likely non-specific, possibly of EBV or lymphocytic or heterophile origin, rather than Fc μ receptors, since another rabbit IgM anti-chicken erythrocyte antibody does not bind, nor does heat-aggregated IgG bind. 100% of the cells are stained with either monoclonal antibodies specific for detecting Ia-like antigen (Lampson, L. A. and Levy, R. Journal of Immunology 125:293–299 (1980)), or having a comparable specificity described as "anti-DR framework" reactivity with B and monocyte precursors (Grumet, F. C. et al, Journal of Immunology 125:2785–2789 (1980)). Polyclonal rabbit anti-β-2-microglobulin antisera reveals 100% membrane binding with goat anti-rabbit FITC. No reactions are observed using a wide variety of other mouse monoclonal antibodies.

Although Pokeweed mitogen (PWM) stimulation was unrewarding for the plaque assay, the cells were tested in a semi-microblastogenesis study (Webel, M. L. et al, American Journal of Clinical Pathology 64:41–47 (1975)) using quadruplicates of phytohemagglutinin (PHA), PWM, concanavalin A (con A), and lipopolysaccharide from E. coli, 0127:B8$^1$ in several concentrations. The nonstimulated control cells incorporated $100,341 \pm 891$ cpm $^3$H- thymidine, the mitogen stimulated cells were all within 2,000 cpm of this non-stimulated response. HLA typing demonstrates that the cells are A1, 33/31; B7, 18: DRW 1,2.

Several karyotyping studies were done, in each of which about 30 metaphases were analyzed by GTG banding (Sealbright, M. Lancet 2:971–972 (1971)). In the eight passage (1977), 2 metaphases were found to have translocations reported as 45, XY,+(2:12) (q37; p13) which were noted on a repeat study. Consequently, the possible significance of this finding representing an abnormal clone or simply an artifact is not known with certainty. Karyotyping of the 55th passage in 1979 revealed 1 metaphase with an abnormal chromosome, 1q three hyperdiploid metaphases of about 90 chromosomes, and 3 hypodiploid cells of 45 chromosomes, each missing a different chromosome ($-1, -12, -21$), and another with $-10, -15, -17, -Y$. Given the differing abnormalities of these defects, they were interpreted to be a result of technical or procedural errors and it is concluded that the cells are normal 46, XY.

The cell line was shown to be of human origin by isozyme identity to human standards at five human loci: LDHA, LDHB, NP, MPI and SOD2, (O'Brien, S. J., Shannon, J. E., and Gail, M. H., In Vitro, 16, 119-135 (1980)). The allozyme genetic signature of the line, which represents the composite isozyme phenotype at eight polymorphic human loci was as follows: PGM1-1, PGD-A, PGM3-1, GLO-1-2, ESD-1, ADA-1, G6PD-B and AK1-1. This phenotype is distinct from HeLa, Raji and other human lymphoid cells examined to date, (O'Brien, S. J., Kleiner, G., Olson, R. and Shannon, J. E., Science, 195, 1345-1348 (1977), O'Brien, S. J., Shannon, J. E., and Gail, M. H., In Vitro, 16, 119-135 (1980)).

Epstein-Barr virus antigens were expressed on cells in passage 2, as well as in the 92nd continuous passage. Early antigen (EA) was found in 0.5-1.0% of the cells. Occasional cells gave a $\pm$ reaction for viral capsid antigen (VCA) with two reference antisera, and all of the cells were positive for nuclear antigen (EBNA) with three positive reference antisera (Reedman, B. M. and Klein, G. Int. J. Cancer, 11, 499-520, (1973), Pearson, G. R., Henle, G. and Henle, W., J. Natl. Cancer Inst., 46, 1243-1250 (1971)). Cultures (Barile, M. F. and Kern, J. Proc. Soc. Exp. Biol. Med., 138, 432-437 (1971)) for mycoplasma in the original and subsequent passages through number 102 have been consistently negative as have biochemical and immunological tests through passage number 150.

The cell line retains excellent viability of greater than 90% after 5 years and more than 150 passages. Recloning by limiting dilution yields cultures having growth, morphologic, and immunological characteristics identical to the original frozen reference cultures.

Two properties of the cell line of the invention can be used advantageously to prepare and selectively separate hybridoma cell lines: 1) The cell line is not a secretory cell line producing IgG or M, and 2) The cell line grows in 3-5% $CO_2$ and is killed in an environment which is 9-11% $CO_2$ or higher.

(1) Basic hybridoma technology requires that the immortalized cell, (e.g., the cell line of the invention), be separated from the fused cell or hybridoma, which becomes immortalized. The antibody-making B-cell that does not fuse is not a problem. Being normal, it dies in 7-14 days in culture. The basic problem is that the immortalized cell line grows orders of magnitude faster than the initially fragile and very slowly replicating fusion, and by sheer numerical advantage makes it near impossible to rescue, find or isolate the hybrid; or the immortalized cell line simply overgrows and kills the hybrid. Because the fusable cell lines available to date are "myeloma" cells and thus secrete IgG, IgM (or rarely IgA) just as the hybrids do, the hybrids and the original cell line cannot be distinguished. However, since the plasmacytoma cell line of the invention is not a secretory cell producing IgG or IgM, it is possible to fuse the cell line of the invention with a human B-cell, and separate the plasmacytoma immediately after fusion by a flourescence activated cell sorter (for example FACS IV ®), since only the monoclonal-antibody generating cells and the B cells will have receptors for IgG or M on their cell membranes. The cell line of the invention does not. Alternatively, one can wait for 2-3 weeks until the B-cell has died and then separate the plasmacytoma from the hybridoma by cell sorting. Although there may be practical problems in carrying this method out to a successful completion, because of the low fusion frequency (very few hybrids are present in the reaction mixture and are therefore not easily separated by the FACS from the several millions of cells of the plasmacytoma of the invention), fluorescence activated cell sorting is clearly a preferred method of separation envisioned by the present inventor. With highly discriminating and highly sensitive FACS ® it should be possible to readily and easily separate the hybrid from the plasmacytoma.

(2) The second useful property of the plasmacytoma is that it is substantially killed in a gaseous environment over the growth medium suspension, which is at least 9-11% $CO_2$ (v/v) in concentration. Since hybridomas are usually and routinely grown in 10% $CO_2$ and they survive, it is readily possible to separate the plasmacytoma from the hybridomas. Hence, by fusing the plasmacytoma with human B cells, and placing the reaction participants in about 9-11% $CO_2$ or higher, it is possible to identify IgG producing hybrids and non-viable plasmacytoma. Although $CO_2$ concentrations higher than 11% still render the cell line of the invention non-viable, such higher $CO_2$ concentrations may render the growth medium too acidic for the hybridoma, and should be avoided.

In any event, both fluorescence cell sorting and $CO_2$ selection seem to be equally successful in the separation. In fact, both methods can be applied sequentially or alternatively, a single time or repeatedly.

It is also possible to mutate the plasmacytoma cell line of the invention to yield an HPRT-, 6-thioguanine (6THG) mutant. Typically, in prior art hybridoma techniques, an HPRT negative mutant (spontaneous or induced by mutagenesis), conveniently identified by its ability to grow in 8-azaguanine (AZG) or 6-THG, will not grow in a special tissue culture medium containing hypoxanthine, aminopterin and thymidine (HAT), but the hybridoma will. This ensures that if the immortalized cell line is fusable, its own survival would be nil in HAT, but its HPRT+ hybrid would replicate, and generate a monoclonal antibody by virtue of its Ig synthetic and secretory mechanism contributed by the fused B-cell mate. The inventor has prepared a HPRT-, 6-THG mutant, and isolated both 8-AZG and 6-THG spontaneous mutants. These mutants of the plasmacytoma can grow under the same conditions as the parent line, and can also be used (as a third alternative) to prepare hybridomas, by fusing the mutants to B-cells, and separating the hybridomas in a HAT medium.

Fusion of the plasmacytoma (or its HPRT- mutant) can be carried out by any of the well known fusion techniques available to the art (see for example the Koprowski et al patents and the Wands et al patent cited supra). For example, human lymphocytes are stimulated or immunized in vitro or in vivo by preparation of an antigen (viral antigen, bacterial antigen, and the like, e.g., hepatitis B surface antigen, hepatitis BE antigen, SV 40 tumor antigen and the like). Route and schedule of administration of the antigen can be carried out intravenously or intraperitoneally or both. The dosage of administration can be between 1 and approximately 50 micrograms per body weight and can be adjusted accordingly. Administration can be in 1 or 2 or more dosages. Alternatively and preferably the B-cells are obtained from a patient with a given disease and who has a high antibody titer to a desired immunogen. B-cells can be obtained from the spleen or from peripheral blood of the human subject, although peripheral blood is preferred as the source (peripheral blood contains about 20% B cells, which can be separated by standard methodology). Blood is preferred since it can be routinely obtained in sterile fashion, is easily testable for sterility and is normally sterile, whereas the spleen is frequently normally contaminated with commensal organisms, and can only be acquired by invasive techniques. Fusion of the human B cells with the plasmacytoma of the invention can be carried out following the method of Kenett et al (Curr. Topics Microbiological Immunol. 81:77, 1978). Plasmacytoma cells are mixed with B-cells, and Polyethylene glycol (PEG) added after the original medium is drained. After incubation with PEG for a short period of time, cells are separated, resuspended in hybridoma medium, plated and grown in 9–11% $CO_2$ atmosphere. Separation can then be carried out by the FACS method (adding appropriately fluorescent labeled antibodies), by maintaining the atmosphere at 9–11% $CO_2$, or (if a mutant is used), by working in an HAT medium. The microtiter wells are screened for positive growth for 10–20 days following the fusion, and hybridoma cell lines can be selected for cloning from the positively identified monoclonal antibody secretors. Cloning can be carried out by normal techniques.

In sum, the cell line is composed of monoclonal, nonsecretory plasmacytoid cells, in its growth cycle about 15% of cells are synthesizing IgGl/κ but are not secreting either heavy or light chains. Because of its stability, viability and other characteristics (it is mycoplasma free), it can be useful not only for the preparation of hybridomas and their attendant monoclonal antibodies, but also for the study of secretory defects.

The human monoclonal antibodies obtained from the hybridomas can be used in passive immunization without fear of immunizing the patient to a foreign serum. They can be used in tumor therapy, as for example in the targeting of toxic drugs: Antibodies to the tissues of a particular organ or to putative specific tumor antigens can be attached to the drug molecules to concentrate the drug's effect. Alternatively, it is possible to produce antitumor antibodies that will themselves attack tumor cells.

Having now generally described this invention, the same will be better understood by reference to specific examples and procedures which are included herein for purposes of illustration only and are not intended to be limiting of the invention unless specified.

METHODS

Source of the cell line

The patient from whom cells were obtained was an 81-year old male referred to the Mayo Clinic (Rochester, Minnesota) in May 1976 with "left-sided heart failure due to anemia" (HCT 25) and "a blood dyscrasia" (41,200 WBC/mm$^3$). The referring physician reported a differential count of 8% neutrophils, 1% eosinophils, 60% lymphocytes and 31% abnormal mononuclear cells which were felt to be either lymphocytes or plasma cells. The bone marrow at that time was interpreted as normal maturation of the myeloid and erythroid series, but with abnormal cells which appeared to be plasma cell-like. The referring physician and pathologist felt that the patient must have a plasma cell dyscrasia and some form of myeloma "probably light chain disease because of absence of monoclonal gammopathy". However, a consulting hematologist and another pathologist interpreted the marrow as a myelomonocytic leukemia rather than a plasma cell disorder and noted that the PAS stain was negative.

On admission to the clinic, the patient was found to have a mass in the proximal right radius and both motor and sensory loss in the right hand. The peripheral blood smears revealed 5% neutrophils, 1% eosinophils, 11.5% monocytes, 43% lymphocytes and 39.5% atypical lymphocytes. Repeated studies demonstrated a hypogammaglobulinemia, principally of IgG (lowest-high values of 3.87–4.11 mg/ml; 47.8–50.7 IU) and IgM (0.13–0.51 mg/ml; 12.4–48.4 IU) with low but within normal IgA (0.34–0.39 mg/ml; 18.2–20.8 IU). No monoclonal immunoglobulins could be found in the serum or urine. On 21 May 1976 an open biopsy of the right radial mass revealed a lytic plasmacytoma involving the radial nerve. Light and electron microscopy demonstrated the atypical cells in the peripheral blood and marrow to be morphologically indistinguishable from those in the bone lesion. Surface membrane Ig (SmIg) staining could not be detected on any of the cells, but 36% of the fixed cells showed cytoplasmic IgG and κ. The patient was diagnosed as having a nonsecretory plasma cell leukemia with plasmacytoma. By 27 May 1976, 82% of his peripheral cells were atypical plasmacytoid cells and blood was obtained for cell cultures. Radiation to the right radius was started and then a regime of melphalan, allopurinol, and methyl prednisolone was started prior to discharge, anticipating two courses of therapy under the supervision of his referring physician.

In August of 1976 the patient returned to the Mayo Clinic for a follow-up examination. At this time few (9.5%) of the atypical cells could be found in the marrow or peripheral blood, but there was pancytopenia and the patient had considerable bone pain. The patient eventually died of acute left-sided heart failure.

Establishment of the Cell Culture

Twenty cc of heparinized (heparin without preservative) venous blood were obtained at the height of the plasma cell proliferation on May 27, 1976. Erythrocytes in the peripheral blood specimens were permitted to rouleaux in the syringe at room temperature. The suspended and buffy coat cells, principally plasma cells, were gently centrifuged out of the plasma at 100×G, the pellet washed twice with 0.87% $NH_4Cl$ and then washed twice with serumless tissue culture medium (TC) RPMI 1640. Using the general grid culture approach of Nilsson et al (Nilsson, K. Int. J. Cancer, 8:432–442 (1971)), approximately $1 \times 10^7$ cells were pipetted onto 1.5×0.5 cm pieces of sterile, absorbable gelatin sponges in 1 ml RPMI 1640 with 20% FCS in sterile tissue culture petri dishes, with an additional 5 mls of TC fluid used to wash the dish. The initial medium was RPMI 1640 and 15% autologous plasma. The TC dishes were placed at 37° C. in a humidified atmosphere containing 4% $CO_2$. Supernatants from these two dishes were harvested every one to three days, centrifuged and the cell pellets redistributed back into the original cellulose pads. On July 6, 1976, the cells were reharvested, placed in RPMI 1640 with 15% fetal calf serum and transferred to 25 cm² sterile tissue culture flasks and subsequently into 75 cm² TC flasks. Active proliferation and cell clumping were observed on July 9, 1976. Unlike Nilsson's method, a fibroblast feeder layer was not employed.

A variety of other media (McCoy's, Eagle's, HEPES or bicarbonate buffered TC 199) with and without the sponges, as well as different concentrations of FCS or human AB serum, also were employed in several but not all possible combinations. None of these cultures yielded more than a sparse initial growth. Subsequently, one ml of the patient's marrow suspension was obtained and separated on a Ficoll-Hypaque gradient (Bøyum, A., Scand. J. Immunol. Suppl., 5:9–15 (1976)), after a 1:1 dilution of TC medium RPMI 1640, and the separated round cells as well as the other neat specimen were plated directly into gelatin sponges comparable to the peripheral blood specimens previously described. No growth could be discerned in these cultures.

The cells grown in suspension formed small clumps which were and remain relatively easy to disperse. Alteration in FCS concentration to 10, 15 or 25% were marginally satisfactory to successful for growth, but the most efficient method yielding the largest number of cells was obtained with 20% FCS at 38° C. in a humid atmosphere of 4% $CO_2$. Cell growth was similar in 0.48% agarose under the same conditions. Optimal cell replication in passing the culture was achieved by adding an equal volume of new media when the original turned slightly acidic and transferring half of the resulting volume into new 75 cm² flasks. Well over 150 continuous passages have been made from earlier passages frozen away. Viability decreases to 72–83% after 160–170 passages have been made as described above and alterations in the concentrations of FCS or $CO_2$ do not seem to materially improve viability. Centrifuging the cells out of TC medium and reseeding in fresh medium appears to preclude this modest decrease in viability as long as a cell density of 0.5 to $1 \times 10^6$/ml is maintained. Aliquots of passages 2, 4, 7, 8, 10 and, thence, every 10–15 passages through 55 have been preserved in liquid nitrogen for comparison studies. There have been no differences observed in cell characteristics of these passages except for a few abnormalities or artifacts seen in the karyotyping studies.

Characteristics of the Line

Figure 2:
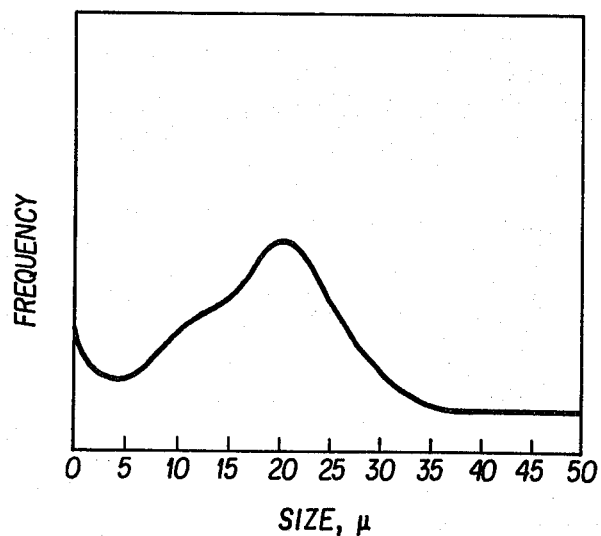
FIG. 2 shows the cell size distribution of CRL-8083 in fluorescence activated cell sorter.

The mean doubling time of the culture is 19.94 hours when the cell concentration is 0.5 to $1 \times 10^6$/ml. The growth characteristics using mithramycin stained cells (0.1 mg/ml in 0.9% saline with 15 mm $MgCl_2$ for 20 minutes) in a fluorescence activated cell sorter is depicted in FIG. 1. Seventy-one and one quarter percent of the cells are in $G_0$ and $G_1$ phases of the cell cycle, 9.81% are in the synthesis (S) phase, and 18.93% are in $G_2$ and M. The cells range in size from 7 to 30μ in diameter but the majority of them are ~20μ in diameter (FIG. 2). There is no correlation between growth cycle phases and a particular cell size. Interleukin-2 has no significant effect on the rate or character of the cell cycle, although two preliminary experiments did suggest a growth enhancement.

The cell line should most preferably be cultured in RPMI 1640/20% FCS with penicillin/streptomycin or gentamycin, optimum cell density $0.5-1 \times 10^6$ and when acid, the medium should be doubled and divided into separate flasks. For freezing, the cell concentration should preferably be at $1-2 \times 10^7$ cell/ml, with final concentration of RPMI 1640/18% FCS, 262.8 micrograms per milimeter of glutamine and 45 micrograms/ml of gentamycin; 1ml/ampoule frozen in vapor phase of liquid nitrogen and submerged for storage can be readily prepared. The cell line was deposited on Aug. 3, 1981 at the American Type Culture Collection.

Source and Enrichment of Human B Cells;

30 cc of heparinized (preservative-free) venous blood were obtained from a volunteer known to have high titers of anti EBV (VCA (viral capsid antigen) 1:160, MA (membrane antigen) 1:320, EA (early antigen) 1:10, EBNA (nuclear antigen) 1:312) antibodies, besides being (professionally) exposed to this virus at the time the sample was drawn. Mononuclear cells were isolated by centrifuging the diluted blood on Ficoll-Hypaque (F/H) cushions. Cells thus obtained were washed twice in Hank's balanced salt solution (HBSS), resuspended in HBSS containing 10% human pooled AB plasma, and 1% heparin before placing them in $13 \times 2$ cm glass petri dishes where they were incubated for 45 min at 37° C. in a 5% $CO_2$ 100% humidity atmosphere. The non-adherent cell fraction was recovered from the plates by pipetting them out and rinsing the dishes with warm (37° C.) HBSS twice. After washing with HBSS, these cells were mixed at a 1:40 ratio with neuraminidase treated sheep red blood cells, incubated for 30 min at 37° C. and for 3½ hours in an ice bath, gently resuspended with a Pasteur pipette and layered and spun on F/H cushions. Cells at the interface were recovered by suction, washed, placed in RPMI 1640 medium containing 10% FCS 2mM glutamine, 5 mg/dl gentamycin, and 50 μg/ml of pokeweed mitogen, and incubated for 24 hours at 37° C. in 5% $CO_2$ for 24 hours prior to use in the fusion. This cell fraction was shown to contain 60–65% surface immunoglobulin positive (SmIg+) cells by means of a standard immunofluorescence assay, and is herein considered as a B cell enriched population.

Fusion Protocol and Outgrowth of Hybrid Cells

The fusion technique used was that described by Kenett et al, (Curr. Top. Microbiol. Immunol. 81:77, 1978). Briefly, $3.5 \times 10^6$ B-enriched cells were mixed with the same number of plasmacytoma cells that were being grown in log phase (generation time ~20 hours). The cell mixture was pelleted, the supernatant drained, and 0.1 ml of a 30% polyethylene glycol (M.W. 950–1050) solution was added for a total of exactly 8 minutes including 6 minutes for centrifugation at room temperature. Cells were washed once, resuspended in hybridoma (HY) medium preferably with 2 μg/dl of ethanolamine and/or "conditioned" medium from human endothelial cells (less than 10% V/V conditioned medium in the HY medium) and distributed in two 96-flat-bottom microtiter plates at an approximate density of $3.5 \times 10^4$ cells per well in 50 μl of medium. Plates were incubated at 37° C. in a 10% $CO_2$ atmosphere, where non-fused CRL-8083 are known to die.

All cultures were fed on day 2, 7 and 10 after the fusion, with 50 μl of HY medium, and by day 12, cells growing in clumps were seen in ~24 of the 192 total wells, while most other wells contained only dead cells and cellular debris, as did the "control" wells containing only B cells.

Screening for Antibody Production

On day 12 after the fusion, supernatants from all wells were removed and transferred to enzyme immunoassay (EIA) microtiter plates, previously coated by physical adsorption with goat anti-human immunoglobulin antibodies. These EIA plates were incubated at 37° C. for 2 hours, washed with PBS-Tween 3X, and filled again with a 1:1000 dilution of an alkaline phosphatase conjugated goat anti-human Ig antibody. After a two hour incubation period, the unbound antibody was washed out, and the presence of specifically bound antibody revealed by the addition of a 1 mg/ml of p-Nitrophenylphosphate solution for 30 minutes.

3/192 supernatants thus analyzed were positive for the presence of human immunoglobulin.

Cloning of Antibody Producing Cells by Limiting Dilution

The cells of those wells where human immunoglobulin was demonstrated were removed by suction, resuspended in HY medium, and counted. Half of them were divided into three fractions, the first of which was cloned out at a 20–25 cells/well density in microtiter plates in HY medium; the second fraction was cloned in the same density and medium in plates in which $5 \times 10^5$ human helper T cells in 50 µl of 0.5% agarose in culture medium had previously been located as feeder layers; and the third was cloned in similar conditions as those described for the first but with the addition of 4 µg/ml of lipopolysaccharide (LPS) B from $E.\ coli$ 0111:B4.

The other half of the cells of the original colonies were stained for SmIg by means of a fluorescin isothiocyanate labeled goat anti-human polyvalent Ig, F(ab')$_2$ preparation, and analyzed, as well as positive cells sorted out, by means of a fluorescence activated cell sorter (FACS IV, Beckton Dickinson, Sunnyvale, Ca). SmIg+ cells, which represented ~85% of the total number of viable cells, were then counted and divided in three fractions each of which was cloned out in the same fashions previously described for non-sorted cells.

Cultures have been maintained at 37° C. in 10% $CO_2$ 100% humidity atmosphere, fed every 6–7 days with HY medium, and observed frequently under an inverted microscope.

Growth is slow and comparable to that observed in murine fusions. However, there are some clump formations found in some wells, particularly in those plates where the medium was added with $E.\ coli$.

Having now fully described this invention, it will be apparent to those of skill in this art that the same can be practiced within a variety of equivalent process and composition parameters without affecting the spirit or scope of the invention or any embodiments thereof.

What is claimed as new and intended to be covered by Letters Patent of the United States Is:

1. A biologically pure cell culture comprising a continuous human, non-antibody-secreting, plasmacytoid cell line having ATCC deposit number CRL-8083 and clones or subclones thereof.

2. A method of producing human-human hybridomas which comprises:
   fusing an antibody producing human B-lymphocyte, with the non-secretory human plasmacytoma of claim 1 to thereby form an antibody-producing hybridoma;
   selecting for said hybridoma in a media containing from about 9% to about 11% carbon dioxide.

3. A method of producing human-human hybridomas which comprises:
   fusing an antibody producing human B-lymphocyte with the non-secretory human plasmacytoma of claim 1 to form an antibody-producing hybridoma;
   mixing the resulting reaction mixture with fluorescent-labeled antibodies thereby allowing said fluorescent labeled antibodies to bind to said hybridoma;
   and separating said hybridomas complexed with said fluorescent antibodies from said non-secretory human plasmacytoma by fluorescence activated cell sorting.

4. The method of any of claims 2 or 3 wherein said hybridoma is cultured in vitro.

5. The method of claim 2 which also comprises admixing the reaction mixture containing the fused hybridomas and the non-secretory plasmacytoma with fluorescent-labeled antibodies thereby allowing said antibodies to bind to said hybridomas and;
   separating said non-secretory human plasmacytoma from said hybridomas carrying said fluorescent antibodies, by fluorescensce activated cell sorting.

6. The method of claim 5 wherein the separation by fluorescence activated cell sorting is carried out prior to the selection in media containing from about 9% to about 11% $CO_2$.

* * * * *